(12) United States Patent
Wetzel et al.

(10) Patent No.: US 7,067,321 B2
(45) Date of Patent: Jun. 27, 2006

(54) POLYGLUTAMINE REPEAT SEQUENCES

(75) Inventors: Ronald Wetzel, Knoxville, TN (US); Wen Yang, Knoxville, TN (US); Valerie Berthelier, Knoxville, TN (US); Songming Chen, Knoxville, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 517 days.

(21) Appl. No.: 10/082,673

(22) Filed: Feb. 22, 2002

(65) Prior Publication Data

US 2003/0162231 A1    Aug. 28, 2003

(51) Int. Cl.
*G01N 33/00*    (2006.01)
(52) U.S. Cl. .......................... 436/86; 436/15; 435/7.1; 435/7.2; 435/7.5; 435/7.92
(58) Field of Classification Search ................ 435/7.1, 435/7.2, 7.92, 7.5; 436/415, 15, 86
See application file for complete search history.

(56) References Cited

OTHER PUBLICATIONS

Biochem. (1999) 38: 8972 by Harper et al.*
Paulson et al. (Neuron 1997 19: 333).*
Protein Science 2001 10: 887 By CHen et al.*
Cell vol. 90, p. 549.*
Perutz, MF, et al., "Glutamine repeats as polar zippers: Their possible role in inherited neurodegenerative diseases", Proc. Nat. Acad. Sci., 91:5355-5358 (1994).
Wetzel, R., "Protein Aggregation *in vivo*", in Stability of Protein Pharmaceuticals: Part B: In Vivo Pathways of Degradation and Strategies for Protein Stabilization, ed. Ahern, TJ and Manning, MC, Plenum Press, New York, pp. 43-88 (1992).
Wetzel, R., "Mutations and off-pathway aggregation of proteins", Trends in Biotechnology, 12(5):193-198 (1994).
Wetzel, R., "For protein misassembly, it's the "I" decade", Cell, 86:699-702 (1996).
Scherzinger, et al., "Self-assembly of polyglutamine-containing huntingtin fragments into amyloid-like fibrils: Implications for Huntington's disease pathology", Proc. Natl., Acad., Sci., 96:4604-4609 (1999).
Scherzinger, et al., "Huntingtin-encoded polyglutamine expansions form amyloid-like protein aggregates *in vitro* and *in vivo*", Cell, 90:549-558 (1997).
Heiser, et al., "Inhibition of huntingtin fibrillogenesis by specific antibodies and small molecules: Implications for Huntington's disease therapy", PNAS, 97(12):6739-6744 (2000).
Sharma et al., "Peptide models for inherited neurologic disorders: conformation and aggregation properties of long polyglutamine peptides with and without interruptions", FEBS Letters, 456:181-185 (1999).
Ester et al., "Aβ deposition inhibitor screen using synthetic amyloid", Nature Biotechnology, 15:258-263 (1997).
Esler et al., "Deposition of soluble amyloid-β onto amyloid templates: With application for the identification of amyloid fibril extension inhibitors", Methods in Enzymology, 309:350-374 (1999).
Bohrmann, et al., "Endogenous proteins controlling amyloid β-peptidepolymerization", J. Biological Chemistry, 274(23):15990-15995 (1999).
Jao, et al., "Trifluoroacetic acid pretreatment reproducibly disaggregates the amyloid β-peptide", Amyloid: Int. J. Exp. Clin. Invest., 4:240-252 (1997).
Zagorski, et al., "Methodological and chemical factors affecting amyloid β peptide amyloidogenicity", Methods in Enzymology, 309:189-204 (1999).
Evans, et al., "Apolipoprotein E is a kinetic but not a thermodynamic inhibitor of amyloid formation: Implications for the pathogenesis and treatment of Alzheimer disease", Proc. Natl. Acad. Sci., 92:763-767 (1995).
LeVine, H, and Scholten, JD, "Screening for Pharmacologic inhibitors of amyloid fibril formation", Methods in Enzymology, 309:467-476 (1999).
Wood, et al., "Selective Inhibition of Aβ fibril formation", J. Biological Chemistry, 271(8):4086-4092 (1996).
Zoghbi, HY and Orr, HT, "Polyglutamine diseases: protein cleavage and aggregation", Current Opinions in Neurobiology, 9:566-570 (1999).
Reddy et al., "Recent advances in understanding the pathogenesis of Huntington's disease", Trends Neurosci., 22:248-255 (1999).

(Continued)

*Primary Examiner*—Long V. Le
*Assistant Examiner*—Jacob Cheu
(74) *Attorney, Agent, or Firm*—Howard Eisenberg, Esq.

(57) ABSTRACT

Several neurodegenerative diseases result from the aggregation of polyglutamine repeat proteins into insoluble neuronal intranuclear inclusions. The invention provides methods with which to study the processes of these diseases, including methods for solubilizing polypeptides containing a polyglutamine repeat sequence, for storing these polyglutamine polypeptides and inhibit their spontaneous aggregation, for making the aggregates of polyglutamine polypeptides, for assaying the extension of existing polyglutamine aggregates, for determining the ability of a chemical compound to inhibit aggregation, and for inhibiting aggregation of polyglutamine polypeptides. The invention further provides materials with which to study these diseases including a synthetic aggregate that have a capability to recruit additional monomeric polyglutamine polypeptides and chemical compounds that inhibit the formation and/or extension of polyglutamine aggregates.

9 Claims, 8 Drawing Sheets

OTHER PUBLICATIONS

Cummings, CJ, and Zoghbi, HY, "Fourteen and counting: unraveling trinucleotide repeat diseases", Human Molecular Genetics, 9(6):909-916 (2000).

Wood et al., "Seeding of Aβ fibril formation is inhibited by all three isotypes of apolipoprotein E", Biochemistry, 35:12623-12628 (1996).

* cited by examiner

$Q_{37}$ Aggregates grown at 37°C (··◇··), and sonicated (··□··), and filtered (··○··)

$Q_{37}$ Aggregates formed at -20°C (-◆-), and sonicated (-■-), and filtered (-●-)

POLYGLUTAMINE REPEAT SEQUENCES

FIELD OF THE INVENTION

The invention relates to the field of diseases that are associated with abnormal aggregation of proteins. Specifically, the invention relates to the field of diseases related to aggregation of intracellular proteins that contain polyglutamine repeat sequences.

BACKGROUND OF THE INVENTION

Insoluble aggregates of normally well-behaved proteins are associated with a variety of disease states, including the various forms of amyloidosis, such as Alzheimer's disease, and the prion diseases such as scrapie and bovine spongiform encephalomyelitis, also known as Mad Cow Disease. A family of proteins, called molecular chaperones, exists in cells to overcome the intrinsic propensity of polypeptides to aggregate during the normal folding process. However, under certain circumstances proteins such as the amyloid β (Aβ) peptide associated with Alzheimer's disease form insoluble protein aggregates in spite of the presence of chaperones. In some amyloid diseases, aggregates appear to be toxic simply by virtue of the effect of their accumulated mass in interfering with normal tissue function. In neurodegenerative diseases like Alzheimer's and Huntington's Diseases, the toxic effect appears to be much more subtle. According to one hypothesis, aggregates become toxic when they clog the cell's normal machinery for clearing aggregates and other superfluous proteins. Another hypothesis holds that aggregate toxicity derives from the ability of aggregates to recruit other essential proteins and in the process deplete the normal environment of their activities. In any case, it would be of considerable value to develop ways of removing these aggregates in a benign way, or preventing their formation, in analogy to the actions of molecular chaperones.

Analogously to the situation in Alzheimer's Disease and Aβ peptide, there are at least eight inherited neurodegenerative diseases, including Huntington's disease (HD), spinal and bulbar muscular atrophy (SBMA), dentatorubral pallidoluysian atrophy (DRPLA), and spinocerebellar ataxias 1, 2, 3, and 6, that are linked to a particular type of protein aggregate.

Although each of these diseases is associated with a different protein, the proteins share the common feature of containing what is referred to as an expanded polyglutamine (poly(Gln)) repeat. These poly(Gln) expansion-related diseases, often referred to as CAG repeat diseases because the glutamine in the poly(Gln) peptide is coded for by the nucleotides CAG, are progressive disorders characterized by motor and/or cognitive impairments and distinctive pathological patterns of neuronal degeneration. The only mutation implicated in these diseases is an expansion of a poly(Gln) sequence in the disease-related protein, generally from a benign length of less than 37 Gln (also referred to as $Q_{37}$) to a pathological length of $Q_{37}$ or more.

All of these neurodegenerative disorders present a common feature: the aggregation of the poly(Gln) repeat disease-related protein into insoluble neuronal intranuclear inclusions, which has become the neuropathological signature of poly(Gln) disorders. The important role that long poly(Gln) repeats play in poly(Gln)-related disorders has been confirmed in a number of models in which mutant forms of various disease proteins were expressed in transgenic mice, *Drosophila*, or the nematode *Caenorhabditis elegans*.

Although these diseases exhibit similar physiological abnormalities, the only common features of disease-related proteins are the poly(Gln) domains. Because of this, the expanded poly(Gln) is believed to be responsible for the pathogenesis. As discussed above, their toxicity is believed to be due to their ability to recruit other critical cellular proteins, via their own poly(Gln) components, into the growing aggregate. The loss of protein activity due to this sequestration appears to be toxic to the cell.

Much about these poly(Gln) diseases remains to be learned. One problem in studying these diseases is that poly(Gln) peptides having a Gln repeat of more than $Q_{35}$ are poorly soluble when transferred directly into denaturing solvents or water. In some circumstances, such as described in Sharma, FEBS Letters, 456:181–185 (1999), the insolubility of long poly(Gln) repeats has presented such an insurmountable problem that studies had to performed on shorter soluble poly(Gln) repeats such as $Q_{22}$, even though mutant proteins involved in the spino-cerebellar ataxia type 1 (SCA) are at least $Q_{40}$.

One method to increase the solubility of monomeric (non-aggregated) Aβ peptide, as disclosed in Evans et al., Proc. Natl. Acad. Sci., 92:763–767 (1995), is to dissolve the peptide in a non-volatile disaggregating solvent such as dimethyl sulfoxide (DMSO). This method has the disadvantage in that the DMSO remains as a permanent co-solvent in the final reaction mixture. Therefore, any results obtained in studies of Aβ peptide dissolved in this way may be biased by the presence of the DMSO.

Use of a volatile disaggregating solvent, trifluoroacetic acid (TFA), to solubilize the Aβ peptide is disclosed in Jao et al., Amyloid: Int. J. Exp. Clin. Invest., 4:240–252 (1997). Volatile disaggregating solvents have an advantage over non-volatile solvents such as DMSO because they are readily removed from the peptide, and thus do not interfere with studies on the peptide. According to this method, TFA is added to the peptide in a glass container at about a 1:1 ratio (ml TFA:mg peptide). Then the TFA and peptide are sonicated, while adding additional TFA, until the peptide completely dissolves. The TFA is then removed with dry nitrogen gas, leaving a coating of peptide on the walls of the container. Trace amounts of the TFA are removed by adding distilled hexafluoroisopropanol (HFIP), sonicating, and removing the HFIP with dry nitrogen gas. Sequential TFA-HFIP treatment has also been disclosed in Zagorski et al., Meths. Enzymol., 309:189–204 (1999). In this protocol, the role played by HFIP seems to be to simply aid in the removal of TFA, which otherwise will make an aqueous solution of the processed peptide acidic and possibly encourage its reaggregation. In our laboratory, this protocol was determined to be effective at solubilizing and disaggregating peptides in the range of $Q_{15}$–$Q_{35}$ However, it is poorly effective with peptides greater than $Q_{35}$.

The inability to dissolve and disaggregate poly(Gln) of the pathological length of $Q_{37}$ or more represents a major obstacle in studying poly(Gln) diseases. A substantial need exists for a method to solubilize and to disaggregate these peptides, and to maintain these peptides in the disaggregated monomeric state.

Another impediment to the study of poly(Gln) aggregation diseases has been the difficulty in making the aggregates in vitro. Typically, as disclosed by Scherzinger et al., Cell, 90:549–558 (1997) and Scherzinger et al., Proc. Natl. Acad. Sci., 96:4604–4609 (1999), such aggregates are made by recombinantly producing a fusion protein (GST-HDex1) containing glutathione S-transferase and exon 1 of the HD (Huntington's Disease). When the fusion protein is cleaved with trypsin, a high molecular weight protein aggregate with a fibrillar or ribbon-like morphology similar to those found in scrapie and in Alzheimer's disease are formed. These recombinantly produced aggregates do not completely correlate with the natural poly(Gln) disease state.

In the disease state, peptides with poly(Gln) repeat lengths as low as $Q_{15}$ or $Q_{20}$, while of insufficient length to readily spontaneously aggregate, readily add to pre-existing aggregates. As disclosed in Perutz, et al., Proc. Natl. Acad. Sci. USA, 91:5355–5358 (1994), aggregates having such shorter poly(Gln) peptides differ from those seen in Alzheimer's disease. Polyglutamine aggregates made in vitro can adopt a number of morphological forms, each of which may differ in toxic activity. Very little is known for certain about the morphology of the toxic form of polyglutamine aggregates in vivo, but if the recruitment hypothesis is correct, than the aggregates must be especially potent in this activity. Consequently, a substantial need exists for methods to prepare different kinds of poly(Gln) aggregates in vitro in order to identify those that are particularly active in supporting deposition and/or extension of additional polyglutamine peptides.

Given the potential role of poly(Gln) aggregates and poly(Gln) aggregate extension in the pathogenesis of expanded CAG repeat diseases, it is essential to characterize the fundamental aggregation behavior of poly(Gln) sequences. Studies of the aggregation behavior dependence on poly(Gln) repeat length are important to fully understand the correlation between length and disease risk, as well as the rules that control the recruitment of other poly(Gln)-containing peptides and proteins into growing poly(Gln) aggregates. Presently, no assay exists that allows the observation of both the homologous growth of an aggregate as well as the ability of the aggregate to recruit other polyglutamine peptides into the aggregate via its extension. Such an assay would have use as an assay for poly(Gln) aggregation and recruitment and as a screen for aggregation inhibitors as potential therapeutics. The assay would also be capable of detecting "extension-competent" or "seeding-competent" aggregates in tissue and serum samples that might be crucial for diagnosis and for evaluating the role of poly(Gln) aggregates in the disease mechanism.

SUMMARY OF THE INVENTION

In one embodiment, the invention is a method for solubilizing and/or disaggregating a polypeptide. The method of the invention is especially useful for solubilizing and/or disaggregating a peptide that has a tendency to spontaneously aggregate. Such peptides, and aggregates thereof, are found in certain diseases such as prion disease and Alzheimer's disease, and with CAG repeat (poly(Gln)) diseases.

According to this embodiment of the invention, the peptide is combined with a mixture of trifluoroacetic acid (TFA) and hexafluoroisopropanol (HFIP) and the peptide is permitted to dissolve in the mixture. Utilizing a mixture of these two solvents, rather than alone or sequentially as taught in the prior art, has been unexpectedly discovered to increase the solubility of peptides, even those having long repeating sequences, such as poly(Gln) where Q>35, that are otherwise difficult or impossible to dissolve by presently available methods. This permits the subsequent step of removing the TFA and HFIP and then resolubilizing the monomeric peptides in water so that the peptides will be in a useful form. According to this embodiment of the invention, it is preferred but not essential that the poly(Gln) polypeptide to be solubilized contain charged amino acids flanking the poly(Gln) sequence in order to increase its kinetic solubility in aqueous solution, that is the transient solubility of the polypeptide when initially dissolved.

In another embodiment, the invention is a method for storing monomeric peptides that have a tendency to aggregate. According to this method, solubilized disaggregated peptides are snap frozen at a low temperature where freezing occurs essentially instantaneously and stored at a temperature of below –50° C., preferably about –80° C. or lower. If desired, DMSO may be added to the solution containing the monomeric peptides prior to freezing. The presence of DMSO, although not preferred, may further help to prevent aggregation of the peptides.

In another embodiment, the invention is a method for making an aggregate of peptides that are prone to aggregation, such as peptides containing a glutamine repeat sequence. According to this embodiment, an aggregation-prone peptide, such as a polypeptide having a glutamine repeat sequence, which peptide is in solution, is frozen and incubated in the frozen state at a temperature at which aggregate formation may occur, and then thawed, at which point the aggregates are collected. The method of the invention permits the formation of peptide aggregates that are not otherwise obtainable, or that are impractical to produce, by prior art methods, such as poly(Gln) aggregates of $Q_{15}$. If desired, the aggregates thus formed may be further processed by sonication and/or filtration.

In another embodiment, the invention is an vitro-produced aggregate composed of peptides having a glutamine repeat sequence, wherein the aggregate is in the shape of a filament having a diameter of less than 10 nm and a length of less than 100 nm. The aggregate may be produced by the method of the invention for making an aggregate of peptides containing a glutamine repeat sequence. Preferably, there is a multiplicity of aggregates of which the majority of the aggregates in the multiplicity of aggregates are in the shape of a filament having a diameter less than 10 nm and a length of less than 100 nm.

In another embodiment, the invention is an in vitro assay for poly(Gln) aggregate formation and for the extension of existing poly(Gln) aggregates. Present methods of assaying for poly(Gln) aggregate formation depend on measurements of the total mass of an aggregate, and are therefore limited in their ability to provide detailed quantification of heterologous aggregation reactions. The assay of the invention is capable of monitoring the repeat length dependence of heterologous aggregation extension, that is, the ability of a poly(Gln) peptide to assemble into an aggregate of another poly(Gln) peptide.

According to this embodiment, labeled monomeric (non-aggregated) poly(Gln) peptide in solution is added to a support to which are fixed poly(Gln) aggregates so that the monomeric peptide solution contacts the fixed aggregates, and the amount of labeled monomeric peptide that binds to the aggregate is determined, typically by counting the amount of the labeling that remains following removal of any unbound monomeric peptide. Preferably, following the addition of the monomeric peptide to the container, the aggregates and monomeric peptides are incubated for a predetermined amount of time during which time the aggregates and monomeric peptides have an opportunity to bind to one another. Also preferably, at a time following the addition of the monomeric peptide and before the amount of labeling remaining is determined, the container is rinsed to remove any monomeric peptide that does not bind to the aggregates. Preferably, the poly(Gln) aggregates that are fixed to the inner surface of the container are the poly(Gln) aggregates of the invention.

In another embodiment, the invention is a method for determining the ability of a chemical compound to inhibit the expansion of existing poly(Gln) aggregates by either homologous or heterologous extension reactions. According to this embodiment, the assay of the invention is performed wherein a test compound is exposed to either or both of the fixed poly(Gln) aggregates and the monomeric poly(Gln) peptides. In this manner, the ability of the test compound to inhibit the formation of, or the extension of, poly(Gln) aggregates can be determined.

In another embodiment, the method of the invention is a method for inhibiting the formation of, or expansion of, poly(Gln) aggregates. According to this embodiment, a poly(Gln) aggregate is exposed to a chemical compound that has the capability to inhibit the formation of, or the expansion of, poly(Gln) aggregates, which capability is preferably determined by testing according to the assay of the invention, thereby inhibiting the expansion of the poly(Gln) aggregate. Preferably, the chemical compound is a compound, or combination of compounds, that has been determined by the assay of the invention to have the capability to inhibit the formation of, or the expansion of, poly(Gln) aggregates. In the previous sentence, the term "compound" includes homologs and analogs of compounds that have been determined to have the capability to inhibit the formation of, or the expansion of, poly(Gln) aggregates, and which homologs and analogs also have this capability. It is conceived that this method of the invention may be useful in vitro, for example as a research tool to study the formation or extension of polyglutamine aggregates, and in vivo, such as for slowing or preventing aggregation in patients susceptible to or suffering from a poly(Gln) repeat disease, such as Huntington's Disease. For in vivo use, an effective amount of a chemical compound, or combination of chemical compounds, that inhibits the formation or extension of poly(Gln) repeats is administered to a patient in need thereof.

In this specification, when referring to a sample containing a poly(Gln) polypeptide of $Q_N$, "$Q_N$" indicates that the sample contains poly(Gln) polypeptide having a weighted average of N poly(Gln) repeats, where N is an integer.

DETAILED DESCRIPTION OF THE INVENTION

The method of the invention to dissolve and/or disaggregate poly(Gln) peptides overcomes the disadvantage of prior art methods as it permits the dissolution and/or disaggregation of poly(Gln) peptides having a repeat length higher than $Q_{35}$, especially those peptides having a poly(Gln) repeat sequence in the pathological range of $Q_{37}$ or higher. In this specification, when referring to the method and to dissolving and disaggregating, the term "dissolving" refers to dissolving monomeric or aggregated poly(Gln) peptides and the term "disaggregating" refers to disaggregating aggregated poly(Gln) peptides to produce monomeric poly(Gln) peptides. The term "solubilize" as used herein refers to either or both dissolving and disaggregating. The method is suitable to solubilize poly(Gln) peptides having a repeat length of up to $Q_{44}$ and even up to $Q_{51}$ or higher, such as up to $Q_{65}$ or higher.

This method is suitable for dissolving any peptide, and conceivably for disaggregating any aggregate, not just those peptides having a poly(Gln) repeat sequence. For example, the method may be used to solubilize any aggregation-prone peptide, such as the amyloid β peptide or a peptide associated with a prion disease. An aggregation-prone peptide, for purposes of this patent, is a peptide which, following dissolution and during storage in solution at room temperature, spontaneously forms aggregates in solution, which aggregate formation may be determined by detecting an increase in light scattering through the solution within one hour from the beginning of the room-temperature storage. For solubilizing polypeptides having a poly(Gln) repeat sequence longer than $Q_{35}$, it is preferable that the polypeptide contain charged amino acids, such as lysine, on both sides of the poly(Gln) repeat sequence. This has been found to increase the kinetic solubility of the poly(Gln) peptide.

According to this method, rather than using either TFA or HFIP, or a sequential combination of TFA and HFIP, to solubilize a peptide, a mixture of TFA and HFIP is used. It has been surprisingly discovered that even hard to dissolve peptides, such as a peptide having a poly(Gln) repeat sequence higher than $Q_{35}$, and such as peptides that are incompletely soluble in TFA or HFIP separately, are solubilized by the method of the invention.

In a preferred embodiment, the peptide is solubilized in a mixture of TFA and HFIP in a ratio of about 1:1. The ratio of TFA and HFIP does not have to be precise. Any ratio of TFA and HFIP is suitable so long as the two compounds are combined during the peptide-solubilization. Suitable ratios of TFA and HFIP are between 20:1 and 1:20, preferably between 10:1 and 1:10, and most preferably between 5:1 and 1:5, such as 3:1 to 1:3 or 2:1 or 1:2. The most preferred ratio is about 1:1 and best results are expected to be obtained when this ratio is used.

Preferably, the peptide is combined with the TFA/HFIP mixture in a container to provide an initial concentration of about 0.5 mg of peptide per ml of the mixture. However, the initial concentration is immaterial as any concentration of peptide in the mixture is suitable. At concentrations lower than 0.5 mg/ml, typically all of the peptide will solubilize without adding additional TFA and/or HFIP. At a concentration of 0.5 mg/ml or higher, typically additional TFA and/or HFIP may have to be added to completely solubilize the peptide.

Preferably, the peptide/TFA/HFIP mixture is incubated until visual inspection or other determination indicates that the peptide has solubilized. If desired, the mixture may be vortexed or otherwise agitated to speed the solubilization process. Incubation is preferably at room temperature, although the temperature may be higher or lower if desired, with the understanding that solutes tend to dissolve more rapidly at higher temperatures than at lower temperatures.

An additional optional step is to remove the TFA and the HFIP from the peptide. This may be accomplished by any known method to remove volatile solvents from a solution. A preferred method is to remove the solvents under a stream of an inert gas, such as nitrogen or argon to leave a residue of dried peptide on the surface of the container. In so doing, it is preferred to utilize a flow rate of the inert gas that is fast enough to maximize the surface area over which the dried peptide residue is deposited but is not so fast as to lead to splashing of the peptide solution out of the container.

Following removal of the TFA and HFIP, the disaggregated peptides may be resolubilized. Resolubilization is preferably in water, preferably distilled, or in a mixture of water and TFA, or in any other medium in which the monomeric peptide will dissolve. A preferred pH range for resolubilization of peptides containing a poly(Gln) repeat sequence is about 3 to 5, and preferably about 3, as these peptides tend to reaggregate more rapidly as the pH approaches 7 or higher. However, pH higher than 5 may be used for resolubilization if desired.

To verify that all aggregates have been effectively dissolved, the solubilized or resolubilized peptides, preferably from an aliquot of the peptide/TFA/HFIP solution, may be tested with a fluorometer and should exhibit low 90° light scattering comparable to that of water alone or to a solution of monomeric poly(Gln) in phosphate buffered saline (PBS). When testing for complete dissolution of peptides having poly(Gln) repeat sequences, it is preferred that the fluorometer is set to excitation and emission wavelengths of about 450 nm. If scattering is found to be high compared to buffer alone, incubation of the remaining peptide/TFA/HFIP solution should be continued until testing of further aliquots reveals that light scattering has been reduced to background levels. Alternatively, the peptide/TFA/HFIP mixture can be further incubated for several hours, such as up to 4 hours or more, with occasional swirling or other agitation, until complete solubilization is obtained.

Following resolubilization, if any residual aggregates remain or to rigorously ensure that all aggregates have been eliminated, they may be removed, such as by filtration or centrifugation with retention of the supernatant. Additionally, if desired to rigorously ensure that all aggregates are eliminated, only the top portion, for example the uppermost ⅔, of the supernatant may be retained.

The method of the invention for solubilizing peptides has been unexpectedly discovered to have the additional advantage of stabilizing monomeric peptides in solution, that is in inhibiting the aggregation of dissolved monomeric peptides. For example, it has been found that a $Q_{15}$ peptide that has been solubilized directly into a pH 3 aqueous buffer and maintained in this buffer tends to rapidly aggregate when the pH is adjusted to 7.4. However, if the peptide is first treated with the TFA/HFIP combination before solubilizing in the pH3 aqueous buffer, then upon adjusting the pH to 7.4 the peptides will remain in the monomeric state for at least a month or more, even if stored at 37° C. Although such dramatic results may not be attainable with peptides having poly(Gln) repeat sequences longer than $Q_{15}$ which have an increase tendency to aggregate, it is conceived that solutions of these peptides will be more stable if solubilized according to the method of the invention than if solubilized by prior art methods.

Peptides that have a tendency to form aggregates, such as poly(Gln)-containing peptides, generally exhibit a time-dependent aggregation when stored in suspension or solution. This occurs even at low pH such as pH 3 and even at low temperatures below physiologic or room temperature. It has been surprisingly discovered that poly(Gln) aggregates will form during storage in the frozen state, such as between −5° C. or −10° C. and −50° C., and that storage in the frozen state may actually stimulate aggregation. It has been further surprisingly discovered that, according to the method of the invention for storing disaggregated peptides, snap freezing of solubilized peptides, such as with liquid nitrogen, followed by storage at a temperature below −50° C., preferably about −80° C., will inhibit or prevent aggregation and will preserve the disaggregated state of aggregation-prone peptides, such as poly(Gln) peptides, for several months.

According to the method of the invention for making an aggregate, dissolved monomeric aggregation-prone polypeptides, such as dissolved monomeric peptides having a poly(Gln) repeat sequence of at least $Q_{15}$ to $Q_{20}$, preferably of at least $Q_{35}$, and most preferably of at least $Q_{37}$, are frozen, such as at between −10° C. to −50° C. or by snap freezing, such as with liquid nitrogen, dry ice, or dry ice-ethanol. The monomeric peptides may be a homogenous or heterogenous population. For example, the poly(Gln) monomeric peptides may be a homogenous population of peptides having the same poly(Gln) length, such as all $Q_{15}$, $Q_{20}$, $Q_{35}$, or $Q_{37}$ or higher, or may be a heterologous population of peptides having different poly(Gln) lengths, such as a combination of poly(Gln) peptides of $Q_{15}$ and higher. In a preferred embodiment, the monomeric aggregation-prone peptides used to make the aggregates of the invention are poly(Gln) peptides that preferably contain a poly(Gln) sequence of greater than $Q_{15}$.

Optionally, the disaggregated peptides may be centrifuged to eliminate any aggregate seeds before freezing. Preferably, but not necessarily, the frozen peptides are stored in the frozen state, preferably at a temperature between −5° C. to −50° C., for at least a day. Preferably, before freezing, the monomeric peptides had been dissolved by the method of the invention for dissolving peptides.

Following the freezing step, optionally followed by the storing step, the frozen peptides are thawed. Aggregates spontaneously form during incubation while frozen, and to some extent during the freezing process unless snap frozen.

Aggregates formed by this method differ in structure from aggregates formed by prior art methods, such as those that do not include a freezing step in accordance with the method of the invention for making polypeptide aggregates.

Figure 1:
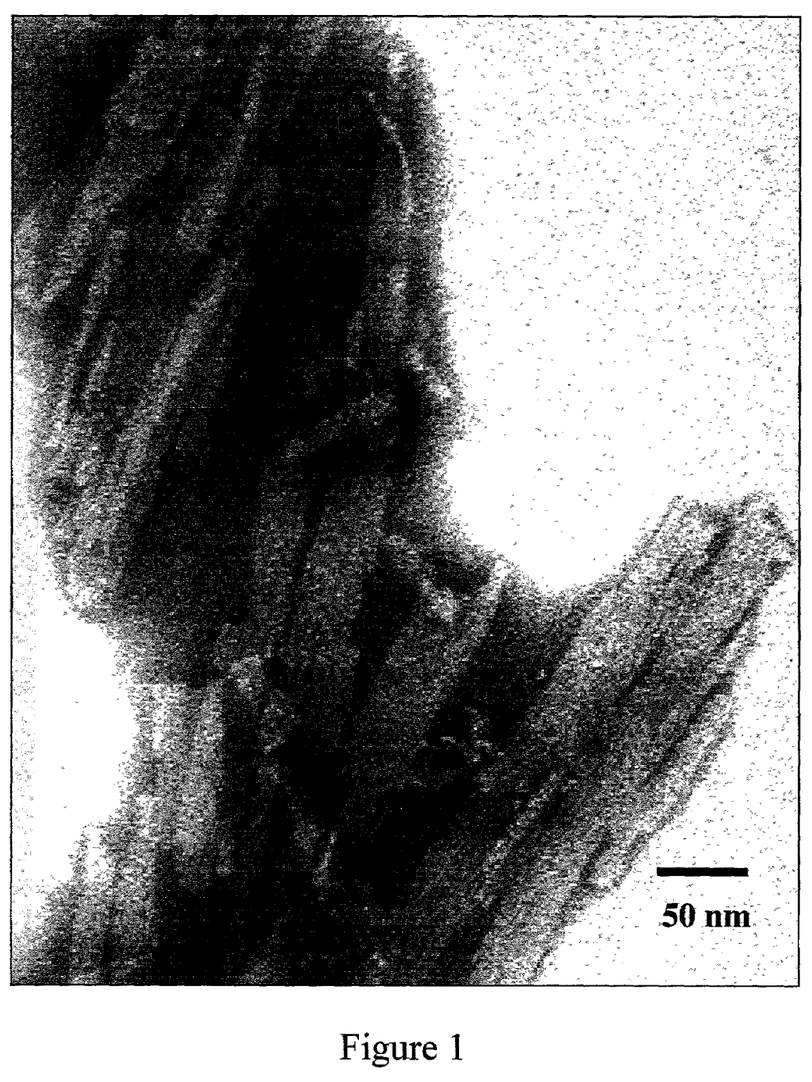
FIG. 1 shows an electron microscopic image of prior art polyglutamine aggregates.
Figure 2:
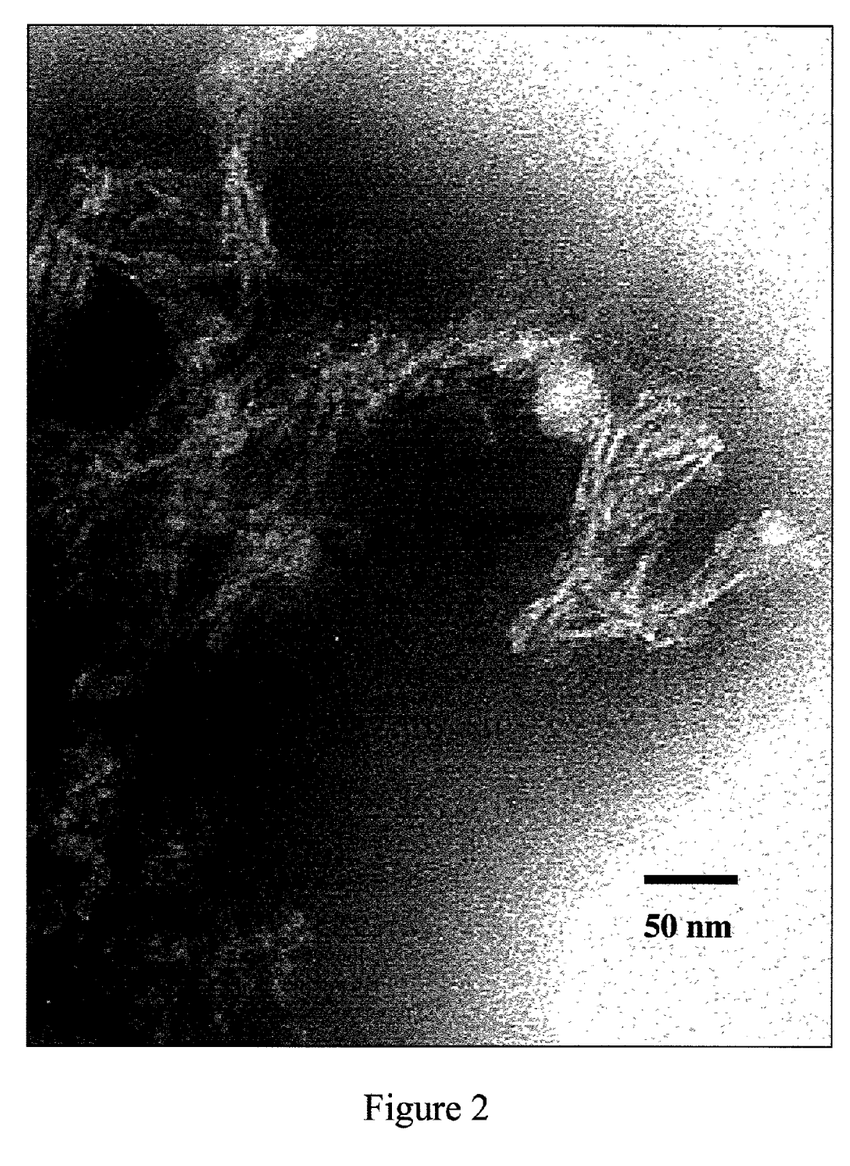
FIG. 2 shows an electron microscopic image of polyglutamine aggregates of the invention.

FIG. 1 and FIG. 2 show an electron microscopic comparison of polyglutamine aggregates formed without a freezing step (FIG. 1) and formed with the freezing step (FIG. 2). The aggregates, as shown in FIGS. 1 and 2 were fixed to mica grids and negatively stained with a 0.25% potassium phosphotungstate solution. The polyglutamine aggregates made with the freezing step are in the form of filaments between 1 and 10 nm in diameter, typically between 2 and 7 nm, and preferably between 2 and 3 nm in diameter. Thus, the polyglutamine aggregates of the invention are between 2% and 20% of the typical 50 nm width of polyglutamine aggregates made without the freezing step. The polyglutamine aggregates according to the invention have a length generally between 20 nm and 100 nm, typically between 30 nm and 75 nm, and preferably between 40 nm and 60 nm, such as 50 nm. Thus, the polyglutamine aggregates of the invention are about 2% to 20% of the typical 500 nm or greater length of polyglutamine aggregates made without a freezing step. The polyglutamine aggregates of the invention made with the freezing step appear to be similar in form to the filamentous components of the aggregates formed without the freezing step. It is conceived that the freezing step prevents the further aggregation of polyglutamine filaments into a longer and thicker conformation.

Figure 7:
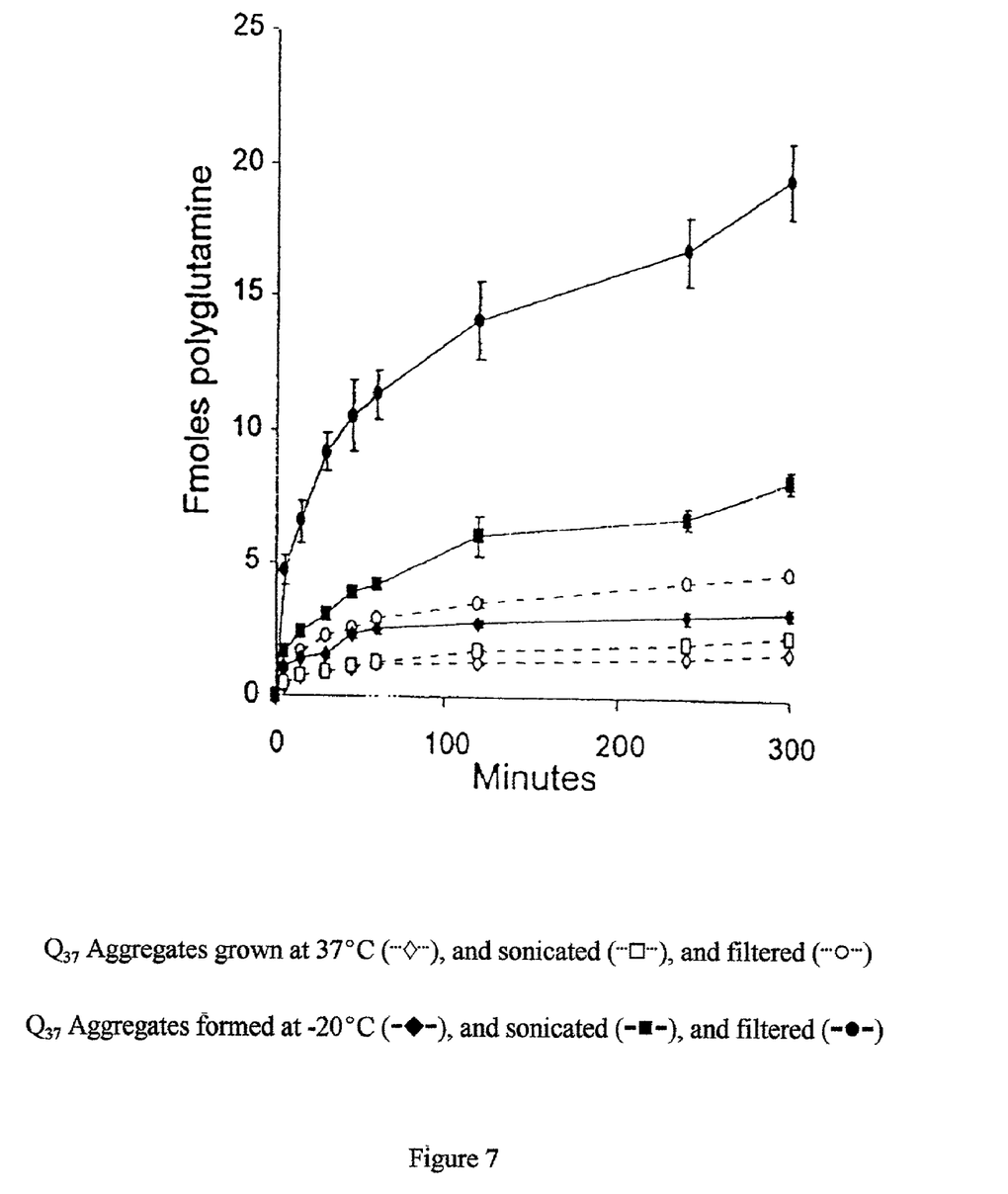
FIG. 7 is a graph showing the effectiveness of aggregates of pathological size ($Q_{37}$) to serve as templates for heterologous extension by other poly(Gln) peptides.

Aggregates of the invention may be, if desired, further processed to produce even finer aggregates. In a preferred method, aggregates of the invention, as described above, are sonicated, such as with a probe sonicator at two minutes at 0° C. The processed aggregates may then be filtered through a membrane, such as between 0.22 µm to 1.2 µm membrane filters, or through a series of membranes, such as sequential 1.2 µm, 0.45 µm, and 0.22 µm filters, to obtain a uniform desired aggregate size. As shown in FIG. 7, aggregates that are sonicated and/or filtered have an increased capability to act as templates for extension by additional poly(Gln) peptides.

The aggregates of the invention, either with or without further processing, are advantageous over prior art aggregates as they are conceived to more closely resemble the polyglutamine aggregates that form in the naturally occurring disease. Additionally, as shown in FIG. 7 and discussed in more detail in the Examples below, the aggregates of the invention, when deposited onto a glass or plastic surface such as a microtiter well, are about 30 times more potent in supporting deposition and/or extension of additional polyglutamine peptides than are the broad ribbon polyglutamine aggregates formed without a freezing step and shown in FIG. 1. This property is believed to be due to an increase in surface-exposed growth points in the aggregates of the invention compared to the thicker and longer prior art aggregates or possibly due to a deleterious change in the local structure of growth points for further aggregation when the filaments are incorporated into the broad aggregates of the prior art.

According to the assay of the invention, poly(Gln) aggregates are immobilized on a surface, such as a microtiter well or a glass or plastic slide, and are then incubated with a labeled monomeric polyglutamine peptide. The degree of adherence, that is addition of monomeric polyglutamine peptides to the bound poly(Gln) aggregates is determined by detecting the amount of label that remains after removal of any unbound monomeric peptide.

The assay of the invention is illustrated below using $Q_{28}$ and $Q_{37}$ aggregates. However, the actual poly(Gln) aggregate that is used is immaterial. For example, the aggregates may have a poly(Gln) repeat from $Q_{15}$ to $Q_{51}$, or may be even longer if desired, for example, up to $Q_{100}$. Aggregate extension by this assay can be observed over a wide variety of poly(Gln) lengths—although some applications may require peptides of a certain length range for optimal performance in a particular application. Additionally, the aggregates may be produced from a combination of poly(Gln) repeat polypeptides, such as $Q_5$, $Q_{20}$, $Q_{25}$, $Q_{28}$, $Q_{35}$, $Q_{37}$, or any other combination. Moreover, the aggregates may be formed of polypeptides in which the major portion of the polypeptide is not a CAG repeat, as is illustrated below with ataxin-3($Q_{27}$).

Preferably, the poly(Gln) aggregates that are fixed to the surface are the aggregates of the invention, or the aggregates made by the method of the invention. These aggregates have been determined to be more efficient at supporting extension reactions, that is recruitment of additional polyglutamine peptides into an existing aggregate, than the broad ribbon-like aggregates of the prior art. However, if desired, prior art aggregates may be used in the assay of the invention.

Monomeric (nonaggregated) polyglutamine peptides are labeled, such as with a radiolabel or with a non-radioactive label such as biotin, and a solution of the monomeric labeled polyglutamine peptides are incubated in contact with the immobilized aggregates. The presence and degree of recruitment of the monomeric peptides onto the immobilized aggregates may be determined by counting the number of labeled peptides that bind to the aggregates, preferably following rinsing to remove any unbound aggregates. From this determination, and with or without knowledge of the concentration of monomeric poly(Gln) peptides that are in the solution, the rate (moles/time) of incorporation of poly(Gln) peptides into poly(Gln) aggregates may be calculated.

The assay of the invention may be used, as described above for studying kinetics of aggregate formation or for discovering inhibitors of aggregate formation, for example. Another use of the assay is for assaying test samples for the presence of aggregates. The assay of the invention is extremely sensitive and is capable of detecting very small quantities of poly(Gln) aggregates by detecting the ability of existing aggregates to recruit additional poly(Gln) peptides. The assay exhibits excellent linearity of response ($r^2$=99), with a sensitivity sufficient to detect as little as 40 pg of a synthetic aggregate. This type of assay may be done, for example, by pouring microplates with different amounts of aggregate per well and testing how well the amount in the wells serves as a matrix for aggregate extension by monitoring the incorporation of subsequently labeled monomer.

This assay may also be used to analyze a tissue extract sample containing an unknown quantity of aggregate. The presence of aggregate in the sample, and possibly the quantification of the amount of aggregate present, may be determined by incubating a dilution of the extract in the microplate well, then assaying with a standard amount of labeled monomer, and reading the signal obtained against a standard curve obtained with synthetic poly(Gln) aggregates, such as those of the invention. In this way, the assay may be used as a diagnostic tool to determine the disease status of a patient, either to follow the progress of a poly(Gln) disease in the patient or to monitor the response of the patient to a therapy.

The assay permits the study of the assembly mechanisms of poly(Gln) aggregates and of critical features of this reaction, such as poly(Gln) length dependence. Another important use of the assay is as a valuable tool in screening and characterizing possible anti-aggregation inhibitors, which inhibitors may be useful therapeutically, and for studying structure-function relationships of the poly(Gln) aggregation reaction, and inhibitors of the reaction, in a clean, well-defined system. In this use of the assay, a known amount of aggregate is bound to a plate, then a known concentration of labeled monomeric poly(Gln) peptide is incubated with the bound aggregate. The assay in this form is capable of detecting femtomole amounts of monomer that become insoluble by binding to the aggregate.

A number of compounds have been detected, by the assay of the invention, to be useful in inhibiting polyglutamine aggregation and/or recruitment of additional peptides into existing polyglutamine aggregates. Compounds that have been determined to be useful in inhibiting such aggregation include polyhydroxy-aromatic compounds such as 6-fluoronorepinephrine, 3-(3,4-dihydroxyphenylserine), α-methylnorepinephrine, benserazide, 2,10,11-trihydroxyaporphine, and 2,10,11-trihydroxy-N-propylnoraporphine, and 2,11-dihydroxy-10-methoxyaporphine. A preferred compound for inhibiting polyglutamine aggregation is myricetin (3,5,7-Trihydroxy-2(3,4,5-trihydroxyphenyl)-4H-1-benzopyran-4-one), disclosed in Merck Index, 9th Ed. entry 6158, pages 821–822 (1976). These and other compounds determined to be useful in inhibiting such aggregation are useful as in vivo pharmaceutical compounds for the treatment of expanded CAG repeat diseases. That is, these compounds may be administered to a patient in need thereof to prevent the extension of existing aggregates in the patient and/or to prevent the formation of aggregates in a patient who is susceptible to forming these aggregates.

The illustrated compounds that inhibit poly(Gln) aggregation share several properties. Each is an aromatic compound containing one or more benzene rings. Each has more than one hydroxyl groups, with at least one of the hydroxyl groups being an aryl hydroxyl. Further several, but not all of these inhibitor compounds, have an amino group that is located at some distance from the at least one of the aryl hydroxyl groups, that is the amino group is not bound directly to the phenyl group to which the aryl hydroxyl group is bound.

The invention and its various embodiments are further illustrated by the following non-limiting examples.

EXAMPLE 1

Solubilization of Poly(Gln) Peptides

Peptides were obtained as unpurified peptides made by custom solid-phase synthesis from the Keck Biotechnology Center of Yale University. The synthetic peptides had a common sequence of a poly(Gln) flanked by pairs of lysine residues ($K_2Q_nK_2$) which bestow a net charge on the peptide at pH 7 to improve initial solubility. Additional biotinylated-$K_2Q_nK_2$ peptides were obtained from the Keck Biotechnology Center for the assay described below in the Examples 8 to 10. The biotinylated peptides were made by N-terminal derivatization during the solid-phase synthesis of the peptides.

1 to 5 mg of peptide as a lyophilized powder from the solid-phase synthesis was combined with a 1:1 mixture of TFA (Pierce, Rockford, Ill.) and HFIP (Sigma, St. Louis, Mo.) to generate a 0.5 mg/ml suspension in a 20 ml Erlenmeyer flask. The suspension was incubated at room temperature with vortexing until visual inspection indicated that the aggregates had dissolved. The suspension/solution was then further incubated for a total time of 0.5 to 4 hours, depending on initial concentration of peptide. The TFA/HFIP solvent was removed at room temperature under a stream of argon gas directed through a Pasteur pipette into the flask. Gas flow was continued for 15 to 30 minutes after visible removal of the solvent. Immediately after gas flow was terminated, distilled water adjusted to pH 3 with TFA was added to the flask to provide a peptide concentration of 100 to 200 µM.

EXAMPLE 2

Testing for Complete Solubilization

Aggregates may persist in the TFA/HFIP mixture after all visible traces of insoluble peptide have disappeared. To check for this, after visually apparent solubilization had been achieved, a test aliquot of the peptide/TFA/HFIP solution was dried under argon and resolubilized as described in Example 1. The dissolution of the aggregates was verified with a fluorometer set to excitation and emission wavelengths of 450 nm. The aqueous 100–200 µM solution exhibited low 90° light scattering comparable to water alone.

If scattering is high, incubation of the main solubilization reaction in the TFA/HFIP is continued, with or without agitation or swirling, until light scattering when measured by fluorometry is reduced to the background level of aqueous buffer alone. If any residual aggregates persist after the peptide has been dissolved in water, such as at pH of about 3, these may be removed by centrifugation and decanting the major portion of the supernatant. Even if no aggregates are apparent, such centrifugation may be advisable to ensure that no aggregates are present.

EXAMPLE 3

No Changes in Peptides Due to TFA/HFIP

To assess whether prolonged exposure of poly(Gln) peptides to the TFA/HFIP solvent combination might introduce any chemical changes in the peptide, samples of the peptide $K_2Q_{15}K_2$ ($Q_{15}$ flanked by two lysines at each end) were incubated overnight at room temperature in a 50:50 mixture of TFA and HFIP and in TFA and HFIP separately. In excellent agreement with the calculated molecular weight of 2453.68, the reconstructed +1 state parent ion of the starting peptide from electrospray mass spectrometry was calculated to be 2352.50. The corresponding reconstructed +1 states after incubating in the three solvent treatments were 2352.40, 2352,40, and 2352.40, respectively. No new fragments were observed in the mass spectra after these solvent treatments.

EXAMPLE 4

Spontaneous Aggregation

Figure 8:
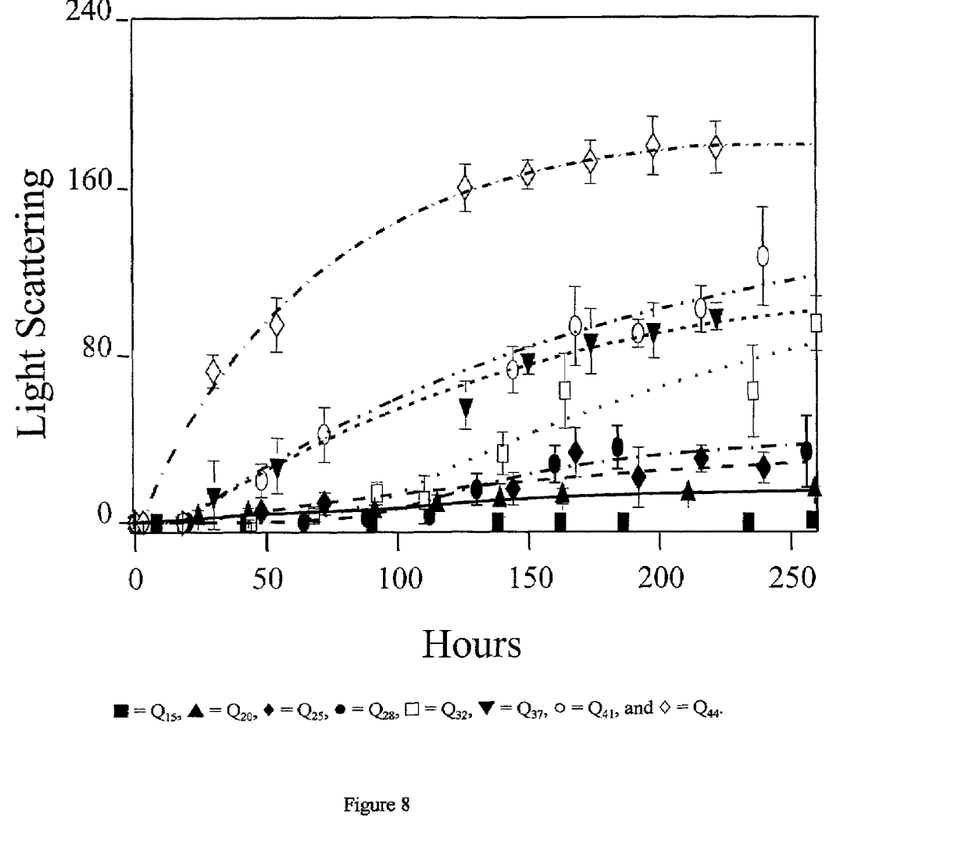
FIG. 8 is a graph showing the solution phase growth of poly(Gln) aggregates.

Poly(Gln) peptide aggregates made of poly(Gln) polypeptides of various lengths were disaggregated and solubilized as described in Example 1 and then incubated at a concentration of 57 µg/ml in PBS at 37° C. Aggregation was monitored by light scattering. The results, as shown in FIG. 8, show that the rate of spontaneous aggregation in solution is related to the length of the poly(Gln) polypeptides.

$Q_{15}$ peptides displayed little tendency to aggregate, exhibiting a lag time of more than 250 hours. Peptides of $Q_{25}$ to $Q_{32}$ have lag times in the range of 25 to 100 hours and the reactions proceed very slowly once aggregation is initiated. As poly(Gln) repeat length increased into the range of $Q_{37}$ to $Q_{41}$, the lag times dropped to about 20 hours and the aggregation reactions proceeded much more rapidly than for the shorter poly(Gln) peptides. Poly(Gln) peptides of $Q_{44}$ showed a lag time of only a few hours and very rapid aggregation reaction following the initial formation of aggregate.

This study was repeated using thioflavin T as described below to monitor the formation of aggregates. The results were essentially identical. The study was repeated with a concentration of 10 µM of the various lengths of poly(Gln) aggregates. Results with identical molar concentrations were similar to results obtained with identical w/v concentrations.

EXAMPLE 5

Prolonged Storage of Solubilized Peptides

Even at pH 3, solubilized peptides exhibit a time-dependent aggregation. To prevent this, following resolubilization, the peptide solution was snap frozen in liquid nitrogen and was stored at −80° C. It was determined that storage at this temperature preserves the disaggregated state of dilute poly(Gln) solutions for several months of storage. Storage at temperatures of about −50° C. or below was found to protect against aggregation. Storage at a temperature of −20° was found to be insufficient to protect against aggregation.

EXAMPLE 6

Preparing Poly(Gln) Aggregates Without a Freezing Step $Q_{37}$ peptides were solubilized as described in Example 1. The solubilized peptides were adjusted to a concentration of 57 μg/ml in PBS and incubated at 37° C. for 7 days. Following this, the concentration of peptide was increased to 10 μM and the aggregates were permitted to grow at 37° C. Aggregation was monitored by thioflavin T fluorescence, as described in Example 7. Aggregates were collected by centrifugation at 20,800×G at 4° C., then resuspended to 44 μg/ml in extension buffer (PBS 1×, 0.01% TWEEN-20 and 0.05% $NaN_3$). The aggregates were fixed to mica grids and negatively stained with a 0.25% potassium phosphotungstate solution, and analyzed by scanning electron microscopy on a Hitachi H-600 electron microscope. See FIG. 1.

EXAMPLE 7

Preparing Poly(Gln) Aggregates of the Invention $Q_{37}$ peptides were solubilized as described in Example 1. The solubilized peptides were adjusted to a concentration of 57 μg/ml in PBS and incubated at 37° C. for 7 days. Following this, the concentration of peptide was increased to 10 μM and was incubated at 37° C. for 24 hours. The aggregates were then snap frozen, followed by further incubation at −20° C. for 24 hours, during which incubation poly(Gln) aggregates spontaneously formed. Aggregation was confirmed by thioflavin T fluorescence, as described in LeVine, "Quantitation of β-sheet amyloid fibril structures with thioflavin T", in *Amyloid, Prions and other Protein Aggregates*, vol. 309, pages 274–284, R. Wetzel, ed., Academic Press, San Diego, Calif. (1999). Thioflavin T was then added to the solution at a concentration of 50 μM, and the fluorescence was determined by excitation at 450 nm (5 nm slit) and emission at 482 nm (10 nm slit). Aggregates were collected by centrifugation at 20,800×G at 4° C., then resuspended to 44 μg/ml in extension buffer (PBS 1×, 0.01% TWEEN-20 and 0.05% $NaN_3$). The aggregates were fixed to mica grids and negatively stained with a 0.25% potassium phosphotungstate solution, and analyzed by scanning electron microscopy on a Hitachi H-600 electron microscope. See FIG. 2.

EXAMPLE 8

Further Processing of Aggregates of the Invention

Some of the aggregates formed by the processes described in Examples 5 and 6 were further processed by sonication with a probe sonicator for 2 minutes at 0° C. or by sonication with a probe sonicator for 2 minutes at 0° C. followed by filtration through a 1.2 μm membrane filter. The filtrate containing small aggregates was retained.

EXAMPLE 9

Preparation of Aggregate Plates

Poly(Gln) aggregates were fixed to activated ELISA microtiter plates (EIA/RIA Plates, Costar, Atlanta, Ga.) by passive adsorption. The microplate was incubated uncovered for 17 hrs at 37° C. with 20 ng of $K_2Q_{28}K_2$ aggregate diluted in 100 μl extension buffer. During this time period the wells were permitted to dry out. After the 17 hrs incubation, the wells were washed 3 times with extension buffer, blocked for 1 hr at 37° C. with 0.3% gelatin in extension buffer, and washed again 3 times. Following this treatment, the plate was used immediately although it can be stored for 1 week at 4° C. with 200 μl of extension buffer in the wells.

EXAMPLE 10

Preparation of Biotinylated Poly(Gln) Peptides

Biotinyl-$K_2Q_{28}K_2$ was solubilized as described above in Example 1. The concentration of the $H_2O$/TFA pH3 biotinyl-$K_2Q_{28}K_2$ solution was determined by comparing to a concentration standard that was established using a $K_2Q_{28}K_2$ solution, whose concentration was determined independently by amino acid composition analysis. The calibrated solution was saved as a standard for HPLC determination of future peptide concentrations.

A known volume of the standard was injected on an HPLC and its elution at A215 to A220, the region of absorbance by the peptide bond, was monitored. From the peak area at this wavelength range a value for the absorbance area per unit mass of peptide. Because all poly(Gln) peptides have absorption characteristics at this wavelength that will be dominated by the poly(Gln) sequence, this "weight extinction coefficient" was used to calculate the weight concentrations of solutions of other poly(Gln) peptides of different length. The biotinyl-peptide was diluted into extension buffer to a final concentration of 10 nM, aliquoted, snap-frozen and stored at −80° C.

EXAMPLE 11

Extension Assay

For each replicate of each time point, the extension/storage buffer was removed from an aggregate-coated well and replaced by 100 μl of 10 nM biotinyl-$K_2Q_{28}K_2$ peptide, after which the plate was incubated at 37° C. Kinetics data was collected by establishing individual time points in reverse temporal order. Thus, biotinyl-poly(Gln) peptide was introduced into three wells (for reactions analyzed in triplicate) and the plate incubated at 37° C. sealed with an adhesive overlay. These wells provide the longest time-point data. At this time, the original extension/storage buffer is retained for all other aggregate-coated wells. At the next appropriate time, the plate was removed from the oven and extension/storage buffer removed and discarded from the next set of wells, and replaced by fresh 100 μl aliquots of 10 nM biotinyl-$K_2Q_{28}K_2$ peptide. The plate was resealed and returned to 37° C. This process was repeated until all time points were added. After a final incubation to provide the reaction time for the last-added (therefore earliest) time point, the entire plate was carried through the process described below to develop and measure the signal.

Extension reactions were stopped simultaneously with 3 washes with extension buffer. After the 96-well plate was washed, it was incubated 1 hr at room temperature with 100 µl per well of a 100 ng/ml europium-streptavidin solution (EG&G Wallac, Gaithersburg, Md.) in extension buffer containing 0.5% BSA. The plate was then washed 3 times with extension buffer and the europium was released from streptavidin by addition of 100 µl of enhancement solution (EG&G Wallac), as described in Hemmila, et al., Europium as a Label in Time-Resolved Immunofluorometric Assays, *Anal. Biochem.*, vol. 137:335–343 (1984). After 5 min, europium was measured by a time-resolved fluorometry as described in Diamandis, Immunoassays with Time-Resolved Fluorescence Spectroscopy: Principles and Applications, *Clin. Biochem.*, 21:139–150 (1988) in a Victor 2 (EG&G Wallac) microtiter plate reader using the programmed parameters for counting europium. Europium counts were converted to fmoles europium using a standard curve obtained with a europium solution obtained from EG&G Wallac. Fmoles of europium was converted to fmoles of biotinylated peptide using the manufacturer's determination of 7 $Eu^{3+}$ ions per streptavidin molecule.

Figure 3:
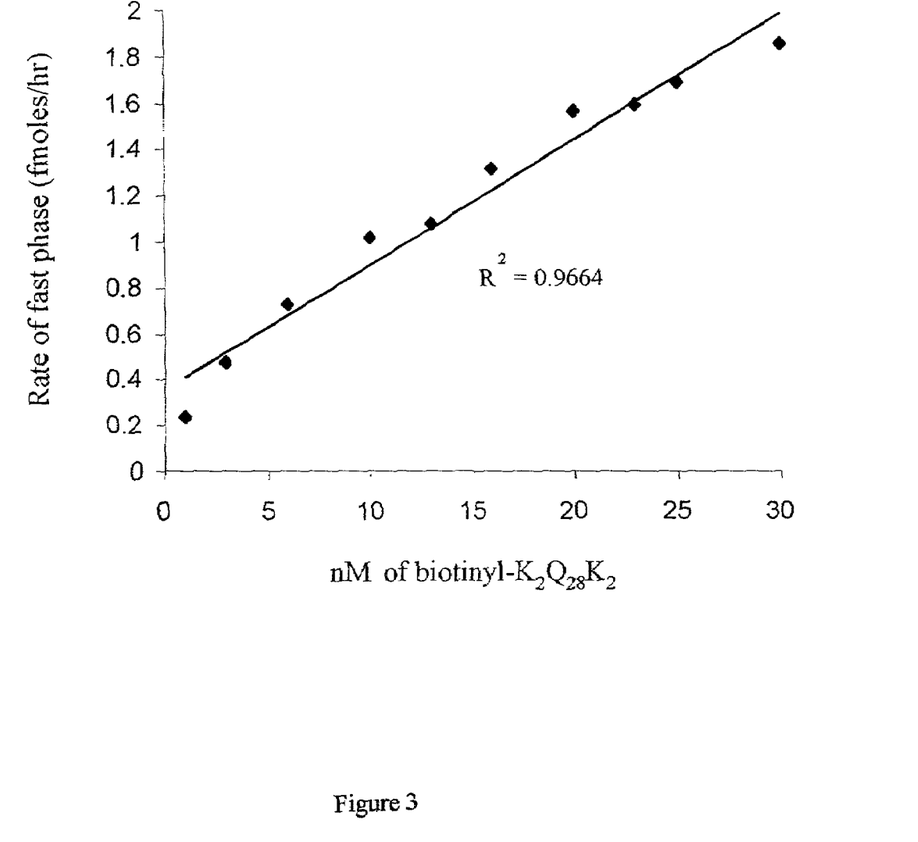
FIG. 3 is a line graph showing the dependence of the rate of the fast phase on biotinyl-poly(Gln) concentration.
Figure 4:
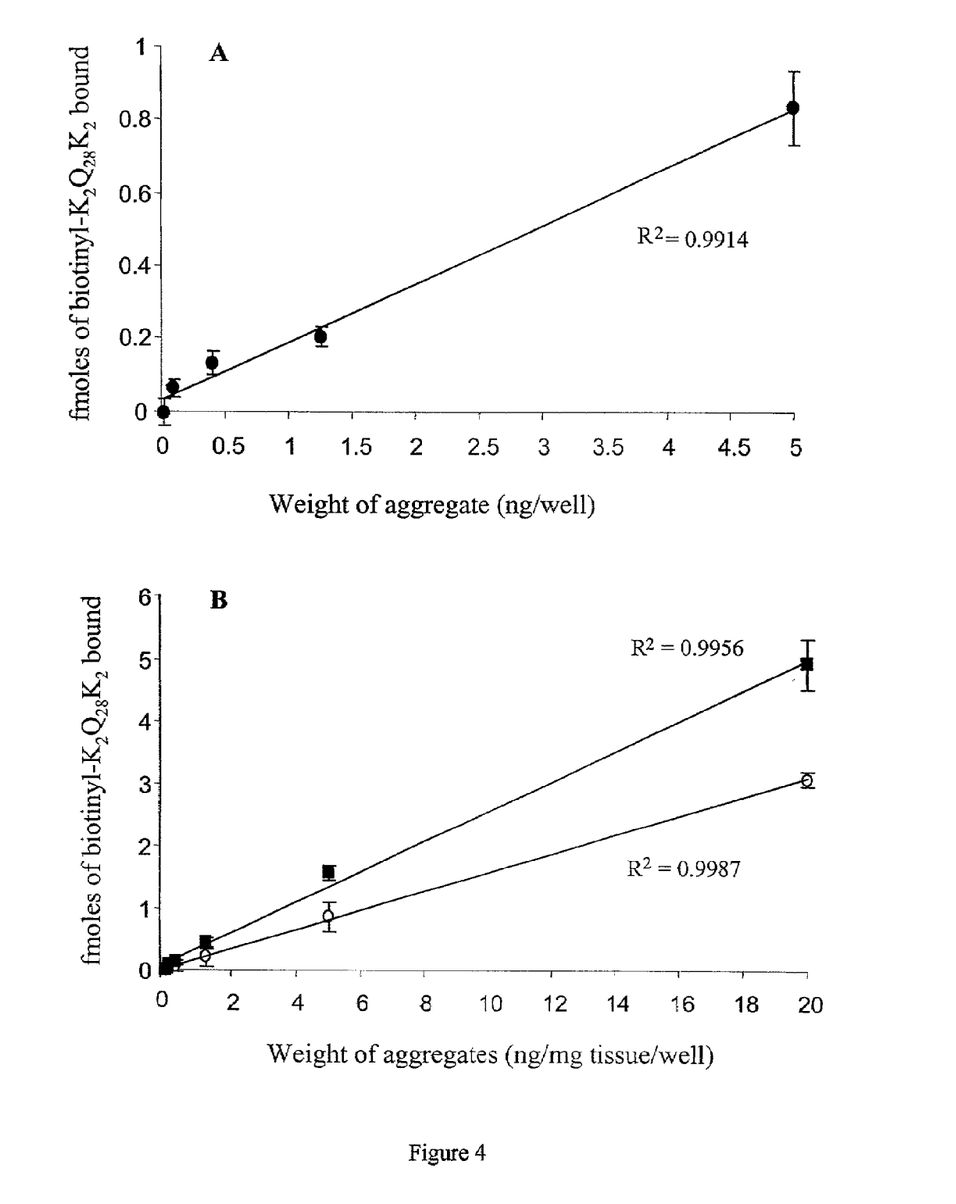
FIG. 4 is a pair of line graphs showing the correlation of the signal strength detected with the amount of poly(Gln) aggregate deposited.

The linearity of the assay of the invention is graphically shown in FIGS. 3 and 4. FIG. 3 is a line graph showing the dependence of the rate of the fast phase on biotinyl-poly (Gln) concentration. 20 ng/well of immobilized $K_2Q_{28}K_2$ aggregates were incubated with biotinyl-$K_2Q_{28}K_2$ in the range from 1 to 30 nM. FIG. 4 is a pair of line graphs showing the correlation of the signal strength detected with the amount of poly(Gln) aggregate deposited in the microplate. In FIG. 4A, various amounts of $K_2Q_{28}K_2$ aggregates were deposited in the microplate in the 25 pg–5 ng range, and incubated 4 hrs with 10 nM of the biotinyl-$K_2Q_{28}K_2$ various amounts of poly(Gln) aggregate ($K_2Q_{28}K_2$). In FIG. 4B, Microplate wells were filled with 100 µl of 780 pg to 200 ng/ml $K_2Q_{47}K_2$ aggregates mixed with 10 mg/ml lipid-extracted brain tissues (○) or with extension buffer (■) and incubated 6 hrs with 100 nM of the biotinyl-$K_2Q_{28}K_2$. Lipid-extracted brain tissue was obtained after sonication and four treatments with chloroform:methanol of small amount of brain tissue ($\leq 0.5$ g) as described (Current Protocols in Molecular Biology, Wiley). The error bars represent the standard deviation of 3 replicates.

To verify that the assay results would not be compromised due to possible biotinyl-peptide dissociation from the aggregates during the europium-streptavidin incubation, a test was run and showed that biotinyl-peptide deposited onto a poly(Gln) aggregate coated well does not dissociate appreciably even after 5 hr at 37° C.

EXAMPLE 12

Assay of the Invention with Monomeric Poly(Gln) Peptides of Varying Lengths

Solutions (10 nM) of disaggregated biotinyl-poly(Gln) peptides of varying lengths from $Q_5$ to $Q_{49}$ were incubated at 37° C. in wells containing immobilized $Q_{37}$ poly(Gln) peptide aggregates. The supernatants were discarded and the wells were washed and incubated at room temperature with a solution of the europium complex of streptavidin. The wells were washed and the deposited europium released into solution with a complexation buffer, then counted by time-resolved fluorescence in a Victor 2 microplate fluorimeter.

Figure 6:
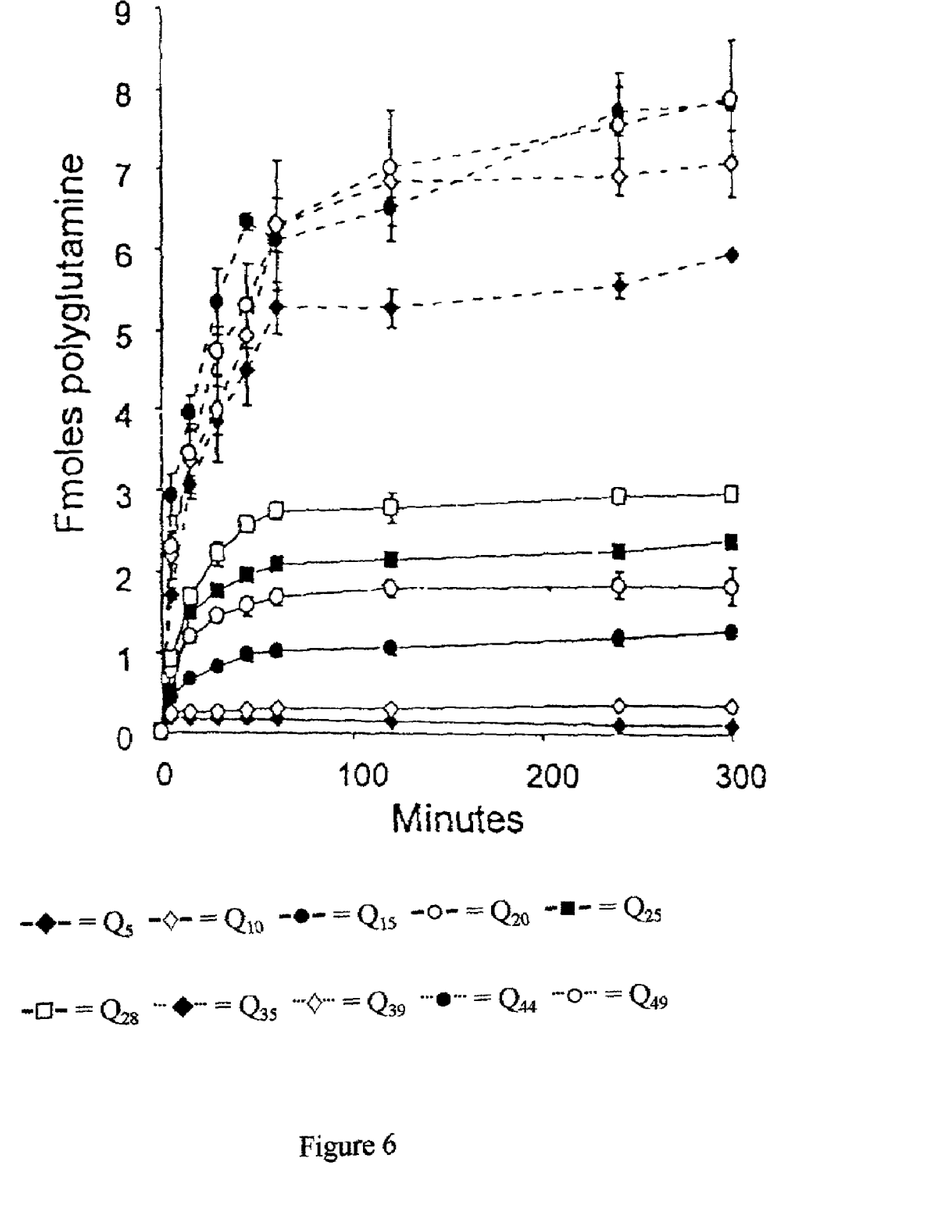
FIG. 6 is a graph showing the relationship of length of poly(Gln) peptides and the capability of the peptides to bind to existing poly(Gln) aggregates.

The results, shown in FIG. 6, show that biotinylated poly(Gln) peptides of different length were readily deposited onto immobilized poly(Gln) aggregates. The results further show that both the amplitude and the rate of the initial, rapid phase of the extension reaction increase with increasing poly(Gln) repeat length.

Peptides with repeat lengths of $Q_5$ and $Q_{10}$ exhibited only a small degree of binding/extension. In contrast, peptides with repeat lengths of $Q_{15}$ and $Q_{20}$ readily added to the pre-existing aggregates. As the poly(Gln) repeat length further increased up to $Q_{39}$, the ability to be recruited into the existing aggregate also increased. Further length increases, represented by the $Q_{44}$ and $Q_{49}$ peptides, did not add measurably to the rate of extension.

Thus, the assay of the invention established that, while poly(Gln) repeat length contributes to extension activity, the repeat length constraints are less severe for aggregate extension than for spontaneous nucleation. See Example 4 above and FIG. 8. In particular, the data shows that peptide elements as short as $Q_{15}$ are sufficient to support the recruitment of a poly(Gln) containing protein by a pre-existing aggregate.

EXAMPLE 13

Assay of the Invention with Aggregates of Differing Structure

The assay of example 11 was repeated except that six different versions of $Q_{37}$ aggregates were immobilized and their capability to support the recruitment of additional monomeric poly(Gln) peptide was tested with a biotinyl-$Q_{28}$ peptide ($K_2Q_{28}K_2$).

FIG. 7 shows that different aggregated states of the same poly(Gln) sequence exhibit dramatically different abilities to serve as templates for heterologous extension by other poly(Gln) peptides. Six different versions of two series of aggregates of the $Q_{37}$ peptide were prepared. One series of aggregates was prepared by incubating peptide at 37° C. to generate the large, ordered aggregates of the prior art shown in FIG. 1. The other series was prepared as described in Example 6 above to produce aggregates of the invention as shown in FIG. 2. Sub-populations of the aggregates of both series were further processed by sonication with or without a following filtration step, as described in Example 7 above. For each of the resultant six aggregate preparations, the weight concentration of aggregates was determined and equal weights of aggregates were fixed to the wells of microtiter plates.

FIG. 7 shows that these aggregates, all derived from the same $Q_{37}$ peptide, very considerably in their abilities to support heterologous extension by a poly(Gln) peptide. The data shown in FIG. 7 establishes that aggregates of the invention, that is, formed with a freezing step, are more efficient in supporting extension than are the aggregates formed without the freezing step. Additionally, the data shows that, within each of the two series, smaller particles are more efficient at supporting extension than are larger ones, as sonicated plus filtered aggregates were more efficient than those that were sonicated without filtering, which in turn were more efficient than non-sonicated aggregates.

EXAMPLE 14

Assaying for Inhibitors of Poly(Gln) Aggregation

EXAMPLE 14A

Screening Assay

Compound libraries were obtained with compounds dissolved in DMSO and arranged in deep-well plates in 96-well format. From these primary compound library collections, "working stock" plates were prepared in which each well contained a compound at a concentration 10 times higher than the desired, final screening assay concentration, in a solvent of 50% DMSO and 50% PBS. In the example, compound concentrations in the "working stock" plate were about 1 mM, so that final assay concentrations were about 100 µM. However, other concentrations can be used.

Assay plates with wells containing fixed polyGln aggregates were prepared as described in Example 9. Wells were filled with 80 µl of extension buffer and 10 µl of the working stock plate-compounds and incubated for 5 minutes. Control wells were also set up containing 80 µl of extension buffer and 10 µl of the 50/50 DMSO/PBS solvent. Additional control wells contained no immobilized aggregates. In the example, each microplate working stock of compounds was tested on three plates developed in parallel, in order to assess the reproducibility of the assay and gain greater confidence in the results. However, single plate or other numbers of replicate plates can alternatively be conducted. After the 5 minute incubation, 10 µl of 100 nM biotinyl-peptide stored in 5% DMSO was added to each well and the plate incubated for 45 mins at 37° C. Extension reactions were stopped with three washes with extension buffer. The signal was then developed as described for the basic extension assay in Example 11.

Data was processed as follows. The fmoles of biotinyl-polyGln bound in the control wells lacking aggregate was subtracted from the signal for all other wells within the plate. The corrected signals for wells containing aggregate but no inhibitor were averaged. The signal for each test inhibitor was divided by this average and multiplied times 100 to generate the percent amount of peptide incorporation compared to control. This value was subtracted from 100 to generate the % inhibition. Finally, for each compound, the % inhibition values from the three replicate plates were averaged and recorded. In the example, compounds delivering 50% inhibition or greater were considered hits. However, in principle any degree of inhibition significantly higher than the apparent inhibition of the bulk of the test compounds can be assigned as a hit. In practice, the value defining a "hit" is sometimes arbitrarily set in order to obtain a desired "hit rate".

EXAMPLE 14B

Determination of the IC50 Values of the Identified Inhibitors.

As described above, 9.15 pmoles/well of synthetic aggregates were immobilized onto each well. After three washes in extension buffer, wells were incubated 5 minutes with various concentrations of a positive compound, the higher concentration starting at 100 µM. Following the 5 minute incubation, 10 µl of 100 nM of biotinyl-polyGln peptides were added for 45 minutes. At the end of the incubation, the plate was washed three times and the rest of the protocol was applied as described above. For each inhibitor, experiments were done in triplicate and the average taken to determine the IC50 value, the concentration of inhibitor required to give 50% inhibition of extension, compared to a control lacking any added compounds.

EXAMPLE 15

Aggregates Associated with Natural Disease

To confirm that the extension reaction observed for chemically synthesized poly(Gln) peptides as described in Example 10 is guided by the same interactions as those operating in the aggregation of disease-related poly(Gln) proteins, aggregates of ataxin-3 (AT3), the protein responsible for Machado-Josef Disease were prepared and tested. Chemically synthesized poly(Gln) peptides shorter than the 35–40 repeat length pathological cutoff are capable of forming ordered aggregates in vitro. See FIG. 8. Similarly, AT3 with a normal length poly(Gln) sequence is known to be capable of aggregating in vitro.

AT3($Q_{27}$) from *E. coli* extracts was purified and allowed to aggregate. A human recombinant expression construct for the GST fusion with ataxin-3 ($Q_{27}$) [AT3($Q_{27}$)], obtained from Dr. H. Paulson (U. of Iowa), contains an IPTG inducible tac promoter and a thrombin cleavage site providing for the efficient removal of the amino terminal GST fusion from the AT3($Q_{27}$) protein. The construct was transformed into the *E. coli* expression strain BL21. The *E. coli* was grown at 37° C. to late log phase (O.D. 600=0.8–0.9) before a 1 mM IPTG induction. Upon induction, the growth temperature was reduced to 32° C. to minimize the deposition of the AT3($Q_{27}$) into insoluble inclusion bodies. The culture was induced for 2 hours before the cells were harvested by centrifugation. The pelleted cells were then resuspended in sonication lysis buffer (50 mM Tris, 50 mM NaCl, and 5 mM EDTA, pH 8) supplemented freshly with 0.15 mM PMSF, 1.46 µM pepstatin A and 2.4 µM leupeptin (Sigma). The cells were subsequently lysed by sonication and the insoluble material removed by centrifugation.

Purification of the AT3($Q_{27}$) protein was achieved through glutathione sepharose spin filtration chromatography (Amersham Pharmacia, Piscataway, N.J.) followed by on-resin cleavage with thrombin (Novagen, Madison, Wis.) to liberate the ataxin-3 from the bound GST fusion protein. As the final purification step, the resultant digest supernatant containing the cleaved ataxin-3 and thrombin proteins was applied to a S-300 sephacryl (Amersham Pharmacia) gel filtration column. The cleaved AT3($Q_{27}$) eluted as a single peak at the void volume of the S-300 column, consistent with an average globular protein molecular weight of greater than or equal to 1,500 kDa. This indicates that the ataxin protein at this stage of the purification is a water soluble aggregate containing at least 30 molecules of AT3.

SDS-PAGE and western blot screenings of the void volume peak revealed a single band at ~42 kDa that was immunoreactive with both an ataxin-3 polyclonal antibody and the polyglutamine specific 1C2 monoclonal antibody (Chemicon, Temecula, Calif.). These fractions were pooled and incubated at room temperature for six days to complete the aggregation process. A sample of the aggregated AT3 ($Q_{27}$) run on SDS-PAGE revealed a trio of SDS resistant, Coomassie brilliant blue staining bands that were unable to be transferred and screened by western blot. Subsequent dot blot screening verified that the aggregates retain immunoreactivity with the 1C2 antibody. The aggregates were pelleted by centrifugation and resuspended in 1x PBS pH 7.4 buffer and stored at 4° C. Microtiter plates coated with aggregated AT3($Q_{27}$) were prepared in analogy to the above protocol described in Example 8 for chemically synthesized poly(Gln) peptides.

Figure 5:
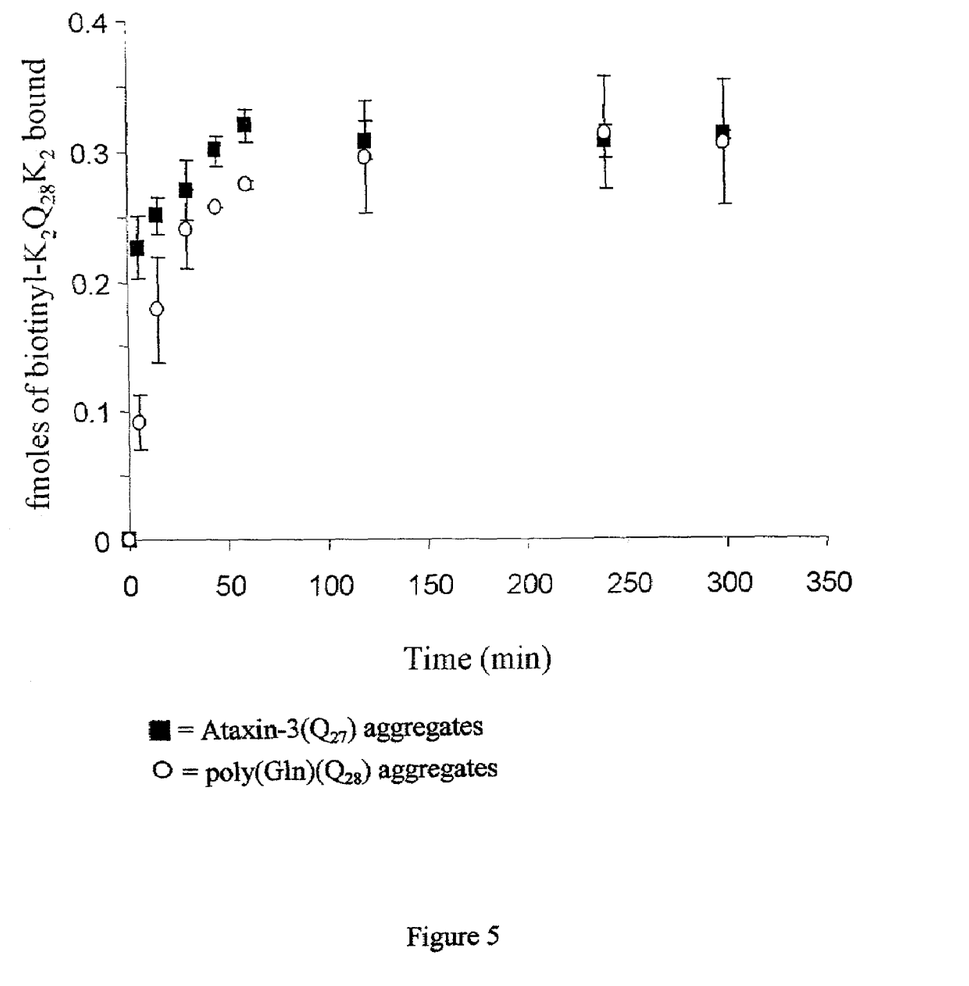
FIG. 5 is a graph showing the correlation between results of the assay of the invention utilizing synthetic poly(Gln) aggregates (circles) and ataxin-3($Q_{27}$) aggregates (squares) found in polyglutamine repeat disease.

The ability of aggregates of AT3($Q_{27}$) to be extended by biotinyl-$K_2Q_{28}K_2$ when the aggregates are fixed to microplate wells was studied. In this study, the amount of AT3 aggregates fixed to the wells was adjusted so that the amount of poly(Gln) on the wells was the same as the amount of aggregated $K_2Q_{28}K_2$ on the same plate. FIG. 5 shows that the kinetics of extension of both aggregates by biotinyl-$K_2Q_{28}K_2$ proceed with similar parameters. This suggests that the in vitro extension process that is observed for the synthetic poly(Gln) aggregates described above is relevant to the natural disease processes of expanded CAG repeat diseases, and that tissue-derived aggregates of disease-associated proteins are observable using the assay of the invention.

Each of the patents and scientific articles cited herein is incorporated herein by reference. Although the above description contains many specificities, they should not be interpreted as limitations on the scope of the invention, but rather as illustrations. One skilled in the art will understand that many variations of the invention are possible and that these variations are to be included within the scope of the following claims.

The invention claimed is:

1. An in vitro produced aggregate comprising a multiplicity of peptides comprising a polyglutamine repeat sequence wherein said aggregate is in the form of a filament having a diameter of between 1 nm and less than 5 nm and a length between 20 nm and 100 nm.

2. The aggregate of claim 1 wherein the diameter is less than about 3 nm.

3. The aggregate of claim 1 wherein the length is less than about 75 nm.

4. The aggregate of claim 3 wherein the length is less than about 60 nm.

5. The aggregate of claim 1 wherein at least one peptide in the aggregate comprises a polyglutamine repeat sequence of at least 16 glutamine residues.

6. The aggregate of claim 1 that has been processed by sonication.

7. A multiplicity of the aggregate of claim 1, wherein the aggregates have been filtered to obtain increased uniformity of size of the aggregates.

8. The aggregate of claim 1 that has been produced by obtaining a solution of non-aggregated peptides containing a polyglutamine repeat sequence, freezing the solution containing the peptides, incubating the peptides in the frozen solution, and permitting the aggregates to form.

9. The aggregate of claim 8 wherein the incubation is at a temperature of between −10° C. to −50° C.

* * * * *